United States Patent [19]

Eberlein et al.

[11] Patent Number: 4,567,178

[45] Date of Patent: Jan. 28, 1986

[54] SUBSTITUTED 5,11-DIHYDRO-6H-DIBENZ[B,E]AZEPIN-6-ONES AND PHARMACEUTICAL COMPOSITIONS CONTAINING SAME

[75] Inventors: Wolfgang Eberlein, Biberach; Günter Trummlitz, Warthausen; Wolfhard Engel; Günther Schmidt, both of Biberach, all of Fed. Rep. of Germany; Rüdolf Hammer; Antonio Giachetti, both of Milan, Italy

[73] Assignee: Dr. Karl Thomae GmbH, Biberach an der Riss, Fed. Rep. of Germany

[21] Appl. No.: 689,325

[22] Filed: Jan. 7, 1985

[30] Foreign Application Priority Data

Jan. 21, 1984 [DE] Fed. Rep. of Germany ....... 3402060

[51] Int. Cl.⁴ .................... A61K 31/55; C07D 403/12; C07D 403/14
[52] U.S. Cl. ............................. 514/215; 260/239.3 T
[58] Field of Search .................. 260/239.3 T; 514/215

[56] References Cited

U.S. PATENT DOCUMENTS

4,308,207 12/1981 Hunziker et al. ................ 260/243.3
4,336,192 6/1982 Steiner et al. ................ 260/239.3 T
4,447,434 5/1984 Trummlitz et al. .......... 260/239.3 T

OTHER PUBLICATIONS

*Chemical Abstracts*, vol. 94, No. 19, May 11, 1981, 156722p.
*Chemical Abstracts*, vol. 95, No. 21, Nov. 23, 1981, 187040q.
*Chemical Abstracts*, vol. 91, No. 23, Dec. 3, 1979, 193150j.

*Primary Examiner*—Robert T. Bond
*Attorney, Agent, or Firm*—Hammond & Littell, Weissenberger & Dippert

[57] ABSTRACT

The invention relates to novel substituted 5,11-dihydro-6H-dibenz[b,e]azepin-6-one of the formula

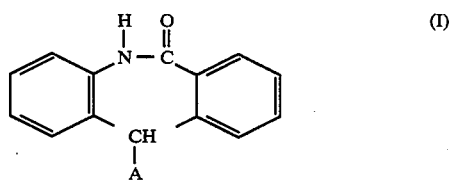

wherein
A represents a (1-methyl-4-piperidinyl)-acetyl, (4-methyl-1-piperazinyl)-acetyl, or [(1-methyl-4-piperidinyl)-amino]-carbonyl group, and the acid addition salts thereof, which have valuable pharmacological properties, particularly an ulcer-inhibiting and secretion-inhibiting activity. The compounds of Formula I may be prepared using methods conventionally used for analogous compounds.

6 Claims, No Drawings

SUBSTITUTED 5,11-DIHYDRO-6H-DIBENZ[B,E]AZEPIN-6-ONES AND PHARMACEUTICAL COMPOSITIONS CONTAINING SAME

The invention relates to novel substituted 5,11-dihydro-6H-dibenz[b,e]azepin-6-ones, processes for preparing them, and pharmaceutical compositions containing these compounds.

German Offenlegungsschrift No. 1,795,176 describes specific dibenzodiazepinones with an ulcer-inhibiting and secretion-inhibiting effect. Substituted dibenzodiazepines with an anti-depressant and analgesic activity are known from U.S. Pat. No. 3,953,430. These compounds have a different ring system, being diazepine derivatives.

It has now been found that certain 5,11-dihydro-6H-dibenz-[b,e]azepin-6-ones have valuable properties which are pharmacologically superior to those of the dibenzodiazepinones or dibenzodiazepines of the above-mentioned publications.

The 5,11-dihydro-6H-dibenz[b,e]azepin-6-ones have the formula

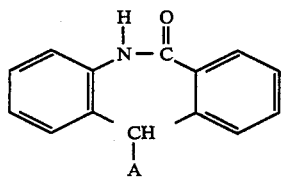

wherein
A represents a (1-methyl-4-piperidinyl)-acetyl, (4-methyl-1-piperazinyl)-acetyl, or [(1-methyl-4-piperidinyl)-amino]-carbonyl group.

After reaction with inorganic or organic acids, the compounds of Formula I may also occur in the form of their pharmacologically acceptable salts. Acids which have proved suitable for this include, for example, hydrochloric, hydrobromic, sulfuric, phosphoric, tartaric, fumaric, citric, maleic, succinic, gluconic, malic, p-toluenesulfonic, methanesulfonic, and amdiosulfonic acids.

The invention relates in particular to the following compounds:
5,11-Dihydro-11-[(1-methyl-4-piperidinyl)-acetyl]-6H-dibenz[b,e]azepin-6-one,
5,11-Dihydro-11-[(4-methyl-1-piperazinyl)-acetyl]-6H-dibenz[b,e]azepin-6-one, and
5,11-Dihydro-11-[[(1-methyl-4-piperidinyl)-amino]-carbonyl]-6H-dibenz[b,e]azepin-6-one
and the pharmacologically acceptable salts thereof.

The invention also relates to pharmaceutical compositions containing one or more dibenzazepinones of Formula I and to the use of said compounds in treating conditions of the gastrointestinal tract in warm-blooded animals or humans.

The substituted dibenzazepinones of Formula I and the acid addition salts thereof have valuable proportions which make them commercially useful. In particular, they are characterized by an excellent protective effect on the stomach and intestines in mammals and, for example, they inhibit the formation of gastric ulcers. Moreover, due to their low toxicity and the absence of any major side effects, they have a favorable therapeutic range.

The excellent activity of the substituted dibenzazepinones of Formula I and/or the pharmacologically acceptable acid addition salts thereof enables them to be used in both human and veterinary medicine, for the treatment and prophylaxis of diseases of the stomach or intestines. For example, they may be used to treat acute and chronic gastric and duodenal ulcers, gastritis, or hyperacid irritable stomach in humans and animals.

If the substituted dibenzazepinones of Formula I according to the invention and/or the pharmacologically acceptable acid addition salts thereof are to be used as active substances for the treatment mentioned above, the pharmaceutical preparations used may also contain one or more pharmacologically active substances from other groups of pharmaceutical products, such as antacids, e.g., aluminium hydroxide or magnesium aluminate; secretion-inhibiting agents such as $H_2$-blockers, e.g., cimetidine or ranitidine; gastric and intestinal therapeutic agents, e.g., metoclopramide, bromopride, or triapride; tranquillizers such as benzodiazepines, e.g., diazepam or oxazepam; spasmolytics, e.g., bietamiverine, or camylofine; anticholinergics, e.g., oxyphencyclimine or phencarbamid; glucocorticoids such as prednisolone, fluocortolone, or betamethasone; non-steroid antiphlogistics such as arylacetic and arylpropionic acids, heteroarylacetic acids, heteroarylpropionic acids, benzothiazine-carboxamide dioxides, pyrazolidine diones, and quinazolinones, e.g., ibuprofen, naproxen, diclofenac, fenbufen, flurbiprofen, indomethacin, lonazolac, sudoxicam, piroxicam, phenylbutazone, calcium bumadizone, or proquazone; local anaesthetics, e.g., tetracaine or procaine; and possibly also enzymes, vitamins, amino acids, and the like. The active substances may be administered to warm-blooded hosts perorally, parenterally, or rectally as active ingredients in customary preparation forms suitable for the intended purposes, that is, compositions consisting essentially of one or more inert conventional carriers and/or diluents, e.g., corn starch, lactose, glucose, microcrystalline cellulose, magnesium stearate, polyvinyl pyrrolidone, citric acid, tartaric acid, water, water/ethanol, water/glycerol, water/sorbitol, water/polyethylene, glycol, propylene glycol, carboxymethylcellulose, or fatty substances such as hard fat, or suitable mixtures thereof, and an effective amount of the active ingredient, such as tablets, coated tablets, capsules, powders, suppositories, syrups, solutions, suspensions, emulsions, infusions, ampules, and drops. Advantageously the active substance or a mixture of different active substances may be administered orally to both humans or animals in a daily dosage generally of from about 0.01 to 5, preferably from about 0.02 to 2.5, more particularly from about 0.05 to 1.0, mg/kg of body weight, possibly administered in the form of several, preferably 1 to 3, dosage units, to achieve the desired results. Dependent upon the type and severity of the affliction, upon the type of preparation, upon the route of administration, as well as upon the period of interval over which the administration takes place, it may, however, be necessary to deviate from the above dosages. Thus, it may be sufficient in some cases to administer more or less than the above-mentioned amounts of active ingredient. The optimum dosage and route of administration of active ingredient necessary in each case can easily be determined by one skilled in the art.

The invention further relates to processes for preparing the dibenzazepinones of Formula I. The compounds of Formula I wherein A represents a (1-methyl-4- piperidinyl)-acetyl or (4-methyl-1-piperazinyl)-acetyl group are obtained by first converting the 5,11-dihydro-6H-benz[b,e]azepin-6-one of the formula

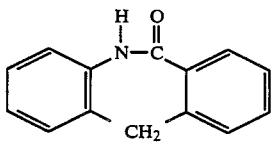

(II)

into its dilithium salt and subsequently reacting the latter with an ester of the formula

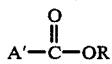

(III)

wherein

A' represents a (1-methyl-4-piperidinyl)-methyl or (4-methyl-1-piperazinyl)-methyl group, and R represents an alkyl group having from 1 to 10 carbon atoms, preferably from 1 to 6 carbon atoms, or an aralkyl group having from 7 to 13 carbon atoms, preferably a phenylalkyl group having from 7 to 9 carbon atoms.

The conversion of the 5,11-dihydro-6H-dibenz[b,e]azepin-6-ones of Formula II into the dilithium salt is carried out with lithium alkyl, but particularly with n-butyllithium, n-butyllithium in the presence of tetramethyl ethylenediamine, tertiary butyllithium, lithium diisopropylamide, or lithium dicyclohexylamide or with lithium aryls, e.g., with lithium phenyl. The conversion into the dilithium salt and the further reaction to form the compounds of Formula I are carried out in an inert organic solvent at temperatures of between −60° C. and ambient temperature, preferably between −10° C. and ambient temperature. The organic solvents used are those conventionally used for reactions with lithium alkyls or lithium aryls. It is particularly advantageous to use tetrahydrofuran or ethers such as diethyl ether, aliphatic hydrocarbons such as hexane, or mixtures thereof, possibly also in the presence of hexamethylphosphoric acid triamide as cosolvent. A short time after the addition of lithium alkyl or aryl has ended, the stoichiometric quantity or a slight excess of the ester of Formula III is added, and the reaction mixture is allowed to return to ambient temperature slowly, e.g., within two hours, to complete the reaction. The product of Formula I formed is isolated from the reaction mixture by conventional methods, and the desired compound is obtained in the form of its base, which can subsequently be converted into the salts thereof, if desired.

The compound of Formula I wherein A represents the [(1-methyl-4-piperidinyl)-amino]-carbonyl group is obtained by reacting reactive derivatives of the carboxylic acid of the formula

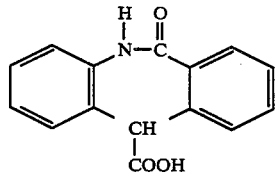

(IV)

with 1-methyl-4-amino-piperidine.

The reactive derivatives of the carboxylic acid of Formula IV used are preferably the acid halides, mixed anhydrides, e.g., with chloroformic acid, the reaction products with N,N-carbonyldiimidazole or with N,N'-dicyclohexylcarbodiimide, but also the esters thereof, preferably with aliphatic alcohols having from 1 to 8 carbon atoms or araliphatic alcohols with from 7 to 13 carbon atoms.

The reaction of the acid halides and anhydrides or of the carboxylic acid of Formula IV with the 1-methyl-4-amino-piperidine is carried out in inert organic solvents or in an excess of this amine and at between ambient temperature and the boiling point of the reaction mixture, preferably at temperatures of from about 40° to 70° C. The solvents used are ethers such as dioxane, tetrahydrofuran, aromatic hydrocarbons such as benzene, chlorobenzene, or toluene, or polar solvents such as dimethylformamide or hexamethylphosphoric acid triamide.

If the work is done with an alkyl chloroformate, the carboxylic acid is suspended in a solvent, e.g., a chlorinated hydrocarbon, preferably in an ester of an aliphatic carboxylic acid in the presence of a base, e.g., a trialkylamine, and the alkyl chloroformate is added while cooling with ice. The 1-methyl-4-amino-piperidine is reacted with the anhydride formed as intermediate product at tempertures of from about 0° to 30° C. The end product is isolated using methods known per se.

The reaction with N,N'-carbonyldiimidazole or N,N'-dicyclohexylcarbodiimide is carried out in inert solvents or suspension agents, preferably in tetrahydrofuran or dioxane, and at temperatures of from about 0° to 100° C., preferably from about 30° to 60° C. The 1-methyl-4-amino-piperidine is then subsequently reacted at these temperatures with the intermediate compounds formed, without previously isolation of them.

The reaction of the esters of the carboxylic acid of Formula IV with the 1-methyl-4-amino-piperidine is also carried out in suitable inert organic solvents, e.g., in aromatic hydrocarbons such as benzene, toluene, xylene, chlorobenzene, or tetrahydronaphthalene, but also in dimethylformamide, dimethylacetamide, or dimethylsulfoxide, in hexamethylphosphoric acid triamide, in ethers such as dioxane or tetrahydrofuran, directly in excess 1-methyl-4-amino-piperidine. The reaction is carried out at temperatures of from about 20° to 180° C., preferably at the boiling temperature of the alcohol released, which is advantageously simultaneously removed by azeotropic distillation.

The dibenzazepinones of Formula I according to the invention contain an asymmetric carbon atom. These compounds may therefore occur in enantiomeric forms. The invention includes the individual enantiomers and the mixtures thereof.

The resolution of any racemates of the compounds of Formula I may be carried out according to known processes, e.g., by use of an optically active acid such as (+)- or (−)-tartaric acid, or a derivative thereof, such as (+)- or (−)-diacetyl tartaric acid, (+)- or (−)-monomethyltartrate, or (+)-camphorsulfonic acid.

According to a conventional method of separating isomers, the racemate of a compound of Formula I is reacted with one of the above-mentioned optically active acids in equimolar quantities in a solvent, and the crystalline optically active salts obtained are separated on the basis of their different solubilities. This reaction may be carried out in any type of solvent provided that the solvent has a sufficient difference in solubility for the salts. Preferably, methanol, ethanol, or mixtures thereof are used, e.g., in a ratio by volume of 50:50. Then, each of the optically active salts is dissolved in water and neutralized, and in this way the corresponding free compound is obtained in the (+) or (−) form. Only one enantiomer is obtained if process described above is carried out with only one enantiomer of Formula IV.

The 5,11-dihydro-6H-dibenz[b,e]azepin-6-one of Formula II used as a starting compound is obtained by heating 2-benzylphenylisocyanate in the presence of anhydrous aluminium chloride [cf., Helv. Chim. Act 48, 336 (1965)]. However, it can also easily be prepared by catalytic hydrogenation from the known morphanthridone.

The carboxylic acid of Formula IV is obtained by oxidation of 5,11-dihydro-11-aldehydo-6H-dibenz[b,e]azepin-6-one with sodium dichromate in glacial acetic acid/sulfuric acid [cf., K. Ackermann et al., Can. J. Chem. 47, 4327, (1969)]. The aldehydo compound is in turn prepared from the known 5,11-dihydro-6H-dibenz[b,e]azepin-6,11-dione (morphanthridone). Alternatively, the carboxylic acid of Formula IV may also be obtained by conventional methods described in the literature by reacting the dilithium salt of the compound of Formula II with carbon dioxide.

As already mentioned, the novel compounds of Formula I have valuable pharmacological properties. In particular, they have anti-ulcerogenic properties and an inhibiting effect on the secretion of gastric acid. They also have favorable effects on various other diseases of the gastrointestinal tract, of which irritable colon should be particularly emphasized.

A favorable relationship between an anti-ulcerogenic and anti-secretory effects on the one hand and the undesirable effects of pupil size and the secretion of tears and saliva, on the other hand, which commonly occur with therapeutic agents having an anticholinergic activity component, is particularly important for the therapeutic use of the substances. The tests which follow show that the compounds according to the invention show particularly favorable characteristics in this respect.

TEST FOR SELECTIVITY OF THE ANTIMUSCARINIC ACTIVITY

Objective

Oxotremorine, a specific agonist at muscarinic receptors, produces lesions of the gastric mucosa in rats and increases the secretion of saliva. This test model was chosen to be able to determine any selective activity of an antimuscarinic substance on the stomach.

Method

Ten female albino rats (of the Crl:COBS-CD(SD) BR strain) with a body weight of from 120 to 150 gm were used for each treatment group. These rats were given free access to drinking water but were deprived of food for 24 hours before the start of the test.

To determine, in preliminary tests, the muscarinic effect of oxotremorine on each of the symptoms investigated, a dosage-activity curve was plotted with at least three doses for each symptom.

When testing antimuscarinic substances, the oxotremorine dosage used was the dosage which triggered the symptom to be influenced in 90 to 100% of the animals in the preliminary tests.

Lesions of gastric mucosa: 0.62 mg/kg i.v.

Secretion of saliva: 0.083 mg/kg i.v.

Each antimuscarinic substance was administered in uniformly graduated dosages by intravenous route 15 minutes before the administration of oxotremorine. Control groups were given the solvent and suspension agent in corresponding amounts instead of the test substance.

Immediately after the administration of the oxotremorine, the animals were observed in a glass cage for 15 minutes.

The test for the influencing of saliva secretion induced by oxotremorine was carried out as a blind test, i.e., the investigator did not known what preliminary treatment the animals had received.

The results were expressed as the percentage inhibition of the oxotremorine effect (percentage of the animals without the symptom in question). The $ED_{50}$ values were determined using the method of LITCHFIELD and WILCOXON (J. Pharmacol. Exp. Ther. 96, 99, 1949).

The effects on lesions of the mucosa in the stomach were evaluated as follows:

The lesions on the gastric mucosa were produced by the intravenous injection of 0.62 mg/kg of oxotremorine 30 minutes after the oral administration of 1 mg/kg of neostigmine (cholinesterase inhibitor). Sixty minutes after the administration of neostigmine, the animals were killed, and the stomachs were removed and opened and checked for the presence of lesions in the mucosa. The protective effect of the test substances was expressed as a percentage inhibition (percentage of animals without lesions). The $ED_{50}$ values were determined using the method of LITCHFIELD and WILCOXON (see above).

MYDRIASIS

The effect of the test substances on the pupil size in rats was investigated as follows:

The substances were administered intravenously to groups of ten animals in at least three uniformly graduated dosages. The pupil size was then observed for ten minutes to see if there were any changes (the occurrence of mydriasis or miosis), and the test was carried out blind, i.e., the investigator was not aware of the preliminary treatment received by the animals. The percentage of test animals in which mydriasis occurred was determined. The $ED_{50}$ values were again determined according to LITCHFIELD and WILCOXON (see above).

MUSCARINIC RECEPTOR BINDING STUDIES

Determination of the $IC_{50}$ value

The organ donors were male Sprague-Dawley rats weighing from 180 to 220 gm. After the removal of the stomach and cerebral cortex, all the other steps were carried out in ice-cold HepesHCl buffer (pH 7.4:100 m molar NaCl, 10 m molr $MgCl_2$). Smooth muscle of the fundic section of the stomach was separated from the gastric mucosa and subjected to preliminary homogenization. All the organs were then homogenized in a potter apparatus.

For the binding test, the homogenized organ preparations were diluted as follows:

Smooth muscle from the funding of the stomach: 1:100.

Cerebral cortex: 1:3000.

The homogenized organ preparations were incubated in an Eppendorf centrifugal tube at 30° C. with a specific concentration of the radioligand and a concentration series of the non-radioactive test substances. The period of incubation was 45 minutes. 0.3N molar $^3$H-N-methylscopolamine ($^3$H-NMS) was used as the radioligand. After the incubation had been stopped by centrifuging at 14,000 g, the radioactivity in the pellet was determined. It represents the sum of specific and non-specific binding of $^3$H-NMS. The proportion of non-specific binding was defined as the radioactivity which was bound in the presence of $1\mu$ molar quinuclidinyl benzylate. Four measurements were taken in each case. The IC$_{50}$ values of the non-labelled test substances were determined graphically. They represent the concentration of test substance at which the specific binding of $^3$H-NMS to the muscarinic receptors in the various organs was inhibited by 50%.

The following compounds
A = 5,11-Dihydro-11-[[(1-methyl-4-piperidinyl)-amino]-carbonyl]-6H-dibenz[b,e]azepin-6-one
B = 5,11-Dihydro-11-[(1-methyl-4-piperidinyl)-acetyl]-6H-dibenz[b,e]azepin-6-one
C = 5,11-Dihydro-[(4-methyl-1-piperazinyl)-acetyl]-6H-dibenz[b,e]azepin-6-one
for example, were investigated as described above. The results of the testing are set forth in the following table:

TABLE

| Compound | Receptor Binding Tests IC$_{50}$ (n Mol l$^{-1}$) | | Oxotremorine Tests ($\mu$g/kg i.v.) | | Mydriasis ED$_{50}$ ($\mu$g/kg i.v.) |
|---|---|---|---|---|---|
| | Cortex | Smooth Muscle from fundus of Stomach | Antiulcerogenic Effect ED$_{70}$ | Inhibition of Salivation ED$_{50}$ | |
| A | 40 | 700 | 22 | 190 | 75 |
| B | 25 | 150 | 13 | 186 | 179 |
| C | 30 | 400 | 80 | 335 | 161 |

The data in the table above show that the compounds mentioned generally have a high affinity for muscarinic receptors. The values also show that the novel compounds of Formula I distinguish between muscarinic receptors of different tissues. This is shown by the considerably lower IC$_{50}$ values in the tests on preparations of the cerebral cortex compared with those obtained from the smooth muscle of the stomach. Also, the pharmacological data in the table show—in complete agreement with the receptor binding studies—that the formation of oxotremorine-induced lesions of the gastric mucosa is inhibited by the compounds of the invention at doses at which no inhibition of salivation and no mydriasis are observed.

The compounds of Formula I are substantially non-toxic even at dosages of over 1000 mg/kg in the mouse.

The following examples are intended to illustrate the invention and should not be construed as limiting the invention thereto.

EXAMPLES

EXAMPLE 1

5,11-Dihydro-11-[(1-methyl-4-piperidinyl)-acetyl]-6H-dibenz[b,e]azepin-6-one

An amount of 25.6 gm (0.06 mol) of n-butyl-lithium (15% in hexane) is added dropwise, at ambient temperature, with stirring, to a solution of 5 gm (0.024 mol) of 5,11-dihydro-6H-dibenz[b,e]azepin-6-one in 70 ml of absolute tetrahydrofuran. The mixture is stirred for 30 minutes at 40° C., and then 11.1 gm (0.06 mol) of ethyl 1-methyl-4-piperidinoacetate are added dropwise to the solution at 5° C. The mixture is stirred for a further 30 minutes, and then the solvent is eliminated in vacuo. The residue remaining is dissolved in a small amount of water, acidified with dilute hydrochloric acid, and extracted again with ether. The ether extracts are discarded. The aqueous phase is made alkaline by the addition of potassium carbonate and extracted exhaustively with chloroform. The combined chloroform extracts are dried with magnesium sulfate and evaporated to dryness in vacuo. The crude product is purified by chromatography on silica gel using a mixture of chloroform/ethyl acetate/methanol as eluant. From the eluate, 950 mg (11% of theory) of the desired compound are obtained, which compound melts at 218°–220° C. after recrystallization from ethyl acetate.

EXAMPLE 2

5,11-Dihydro-11-[(4-methyl-1-piperazinyl)-acetyl]-6H-dibenz[b,e]azepin-6-one

Prepared analogously to Example 1 from 5,11-dihydro-6H-dibenzo[b,e]azepin-6-one and ethyl 4-methyl-1-piperazinoacetate in a yield of 21%.

M.p.: 184°–186° C.

EXAMPLE 3

5,11-Dihydro-11-[[(1-methyl-4-piperidinyl)-amino]-carbonyl]-6H-dibenz[b,e]azepin-6-one A quantity of 2.5 gm (0.01 mol) of 5,11-dihydro-6H-dibenz[b,e]azepin-6-one-11-carboxylic acid is refluxed in a mixture of 50 ml of chloroform and 15 ml of thionyl chloride until totally dissolved. The solvent is then removed in vacuo, and the residue remaining is taken up in 50 ml of dioxane. A mixture of 2.2 gm (0.02 mol) of 4-amino-1-methyl-piperidine in 50 ml of dioxane is slowly added dropwise to this solution, and the resulting mixture is then stirred for 60 minutes at 50° C. It is evaporated in vacuo, the residue is mixed with a small amount of water, and the solution is saturated with potassium carbonate and extracted exhaustively with ethyl acetate. The combined extracts are filtered over active charcoal and then concentrated to dryness in vacuo. The crude product is purified by chromatography on silica gel using methanol as eluant. Colorless crystals, M.p.: 230°–231° C., are obtained in a yield of 1.3 gm (36% of theory).

M.p. (hydrochloride): 306°–307° C. (decomp.).

EXAMPLE 4

5,11-Dihydro-11-[[(1-methyl-4-piperidinyl)-amino]-carbonyl]-6H-dibenz[b,e]azepin-6-one An amount of 1.8 gm (0.01 mol) of ethyl chloroformate is slowly added dropwise, under cooling with ice, to a suspension of 2.5 gm (0.01 mol) of 5,11-dihydro-6-oxo-6H-dibenz[b,e]azepin-11-carboxylic acid and 2.0 gm (0.02 mol) of triethylamine in 150 ml of ethyl acetate. The resulting mixture is stirred for one hour at ambient temperature, and then a solution of 1.25 gm (0.01 mol) of 4-amino-1-methyl-piperidine in 20 ml of ethyl acetate is added dropwise thereto. After being left to stand overnight, the reaction solution is extracted several times with dilute hydrochloric acid, and the aqueous acetic extracts are separated off and neutralized, for example, by the addition of solid sodium bicarbonate. The aqueous solution is exhaustively extracted with ethyl acetate, dried over magnesium sulfate, and concentrated to dryness in vacuo. By digestion of the residue in a small amount of ether, crystals are obtained, M.p.: 230°–231° C., in a yield of 1.8 gm (51% of theory). According to the mixed melting point, thin layer chromatography, and IR spectrum, the substance is identical to the product obtained in Example 3.

EXAMPLE 5

5,11-Dihydro-11-[[(1-methyl-4-piperidinyl)-amino]-carbonyl]-6H-dibenz[b,e]azepin-6-one A quantity of 3.5 gm (0.022 mol) of N,N'-carbonyldiimidazole is added to a suspension of 5 gm (0.02 mol) of 5,11-dihydro-6-oxo-6H-dibenz[b,e]azepin-11-carboxylic acid in 100 ml of tetrahydrofuran, and the mixture is heated to 40° C. for 30 minutes. Then, 2.5 gm (0.022 mol) of 4-amino-1-methylpiperidine are added, and the mixture is heated for a further two hours at 40° C. After cooling, the solvent is removed in vacuo, and the residue is purified by column chromatography on silica gel [ethylene chloride/methanol (9:1)]. Subsequently, 4.8 gm (68%) of the desired compound, M.p.: 230°–231° C., are obtained from the eluate. According to the mixed melting point, thin layer chromatography, and IR spectrum, the substance is identical to the product obtained in Example 3.

EXAMPLE 6

5,11-Dihydro-11-[[(1-methyl-4-piperidinyl)-amino]-carbonyl]-6H-dibenz[b,e]azepin-6-one A suspension of 5 gm (0.02 mol) of 5,11-dihydro-6-oxo-6H-dibenz[b,e]azepin-11-carboxylic acid and 4.5 gm (0.022 mol) of N,N'-dicyclohexylcarbodiimide in 180 ml of tetrahydrofuran is heated to 40° C. for 60 minutes. Then, 2.5 gm (0.022 mol) of 4-amino-1-methyl-piperidine are added dropwise to the reaction solution, which is heated for a further two hours at 40°–50° C. After cooling, the solution is evaporated in vacuo, and the residue remaining is purified by chromatography on silica gel [methylene chloride/methanol (9:1)]. Crystals, melting point of 230°–231° C., are obtained from the eluate in a yield of 3.7 gm (53% of theory). According to mixed melting point, thin layer chromatography, and IR spectrum, the substance is identical to the product obtained in Example 3.

EXAMPLE 7

5,11-Dihydro-11-[(1-methyl-4-piperidinyl)-acetyl]-6H-dibenz[b,e]azepin-6-one

Analogously to Example 1, a solution of 3.0 gm (0.03 mol) of diisopropylamine in 50 ml of tetrahydrofuran and 21.3 ml (0.032 mol, 1.6 molar in hexane) of n-butyllithium is reacted at −10° C. with 2.0 gm (0.01 mol) of 5,11-dihydro-6H-dibenz[b,e]azepin-6-one and 5.5 gm (0.032 mol) of methyl 1-methyl-4-piperidinoacetate.

After the crude product has been purified by chromatography on silica gel, a compound is obtained which, according to the mixed melting point, thin layer chromatogram, and IR spectrum, is identical to the product obtained in Example 1.

Yield: 1.04 gm (30% of theory).

EXAMPLE 8

5,11-Dihydro-11-[(4-methyl-1-piperazinyl)-acetyl]-6H-dibenz[b,e]azepin-6-one

Prepared analogously to Example 1 by reaction of 10 gm (0.048 mol) of 5,11-dihydro-6H-dibenz[b,e]azepin-6-one, 50 gm (0.12 mol) of phenyllithium (20% in benzene/ether), and 20.5 gm (0.096 mol) of butyl 4-methyl-1-piperazinoacetate in 200 ml of absolute tetrahydrofuran, in a yield of 4.2 gm (25% of theory).

According to the mixed melting point, thin layer chromatogram, and IR spectrum, the resulting compound is identical to the product obtained in Example 2.

EXAMPLE 9

5,11-Dihydro-11-[(1-methyl-4-piperidinyl)-acetyl]-6H-dibenz[b,e]azepin-6-one

Prepared analogously to Example 1 by reaction of 5.0 gm (0.024 mol) of 5,11-dihydro-6H-dibenz[b,e]azepin-6-one and 38 ml (0.06 mol) of n-butyllithium (1.6 molar in hexane) with 11.9 gm (0.048 mol) of benzyl 1-methyl-4-piperidinoacetate in 100 ml of absolute tetrahydrofuran, in a yield of 1.7 gm (20% of theory).

According to mixed melting point, thin layer chromatogram, and IR spectrum, the compound is identical to the product obtained in Example 1.

The following examples illustrate a few pharmaceutical compositions comprising a compound of the present invention as an active ingredient and represent the best modes contemplated of using the invention. The compound 5,11-dihydro-11-[[(1-methyl-4-piperidinyl)-amino]-carbonyl]-6H-dibenz[b,e]azepin-6-one has been used as the active substance. However, it should be understood that one or more other compounds of Formula I or pharmacologically acceptable acid addition salts thereof can be used as active substance in place of said compound.

EXAMPLE 10

Tablets containing 25 mg of Active Substance

Each tablet has the following composition:

| Component | Amount (mg) |
| --- | --- |
| Active substance | 25.0 |
| Lactose | 148.0 |
| Potato starch | 65.0 |
| Magnesium stearate | 2.0 |
| Total: | 240.0 |

Preparation

A 10% mucilage is prepared from potato starch by heating. The active substance, lactose, and remaining potato starch are mixed together and granulated with the mucilage through a 1.5 mm mesh screen. The granulate is dried at about 45° C., passed through the screen again, and mixed with magnesium stearate. The finished mixture is compressed in a tablet press using punches 9 mm in diameter to form tablets.

Weight of tablet: 240 mg.

EXAMPLE 11

Coated Tablets containing 25 mg of Active Substance

The tablets prepared according to Example 10 are covered in known manner with a coating consisting essentially of sugar and talc. The finished coated tablets are polished with beeswax.

Weight of tablet: 300 mg.

EXAMPLE 12

Ampules containing 1.0 mg/ml of Active Substance

Each ampule contains the following:

| Component | Amount |
| --- | --- |
| Active substance | 1.0 mg |
| Sodium chloride | 8.0 mg |
| Distilled water q.s. ad | 1.0 ml |

Preparation

The active substance and sodium chloride are dissolved in distilled water and then made up to the given volume. The resulting solution is filtered under sterile conditions.

Bottling: in 1 ml ampules.

Sterilization: 20 minutes at 120° C.

EXAMPLE 13

Suppositories containing 5 mg of Active Substance

Each suppository has the following composition:

| Component | Amount (mg) |
| --- | --- |
| Active substance | 5.0 |
| Suppository mass (e.g., WITEPSOL ® H19 or W45, available from Chemische Werke Witten GmbH) | 1695.0 |
| Total: | 1700.0 |

Preparation

The suppository mass is melted, and after the molten mass has been cooled to 40° C., finely powdered active substance is homogeneously suspended therein. The molten mass is then cooled to 37° C. and poured into slightly chilled suppository molds.

Weight of one suppository: 1.7 gm

EXAMPLE 14

Drops containing 5 mg/ml of Active Substance

One hundred milliliters of drop solution has the following composition:

| Component | Amount |
| --- | --- |
| Active substance | 0.5 gm |
| Methyl p-hydroxybenzoate | 0.035 gm |
| Propyl p-hydroxybenzoate | 0.015 gm |
| Anisole | 0.05 gm |
| Menthol | 0.06 gm |
| Pure ethanol | 10.0 gm |
| Sodium cyclamate | 1.0 gm |
| Glycerol | 15.0 gm |
| Distilled water q.s. ad | 100.0 ml |

Preparation

The active substance and sodium cyclamate are dissolved in about 70 ml of water, and the glycerol is added. The p-hydroxybenzoates, anisole, and menthol are dissolved in ethanol, and this solution is added to the aqueous solution with stirring. Finally, the mixture is made up to 100 ml with water and filtered to remove suspended particles.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A compound of the formula

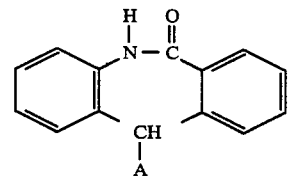

wherein

A represents a (1-methyl-4-piperidinyl)-acetyl, (4-methyl-1-piperazinyl)-acetyl, or [(1-methyl-4-piperidinyl)-amino]-carbonyl group, or an entantiomer or pharmacologically acceptable addition salt thereof with an inorganic or organic acid.

2. The compound of claim 1 which is 5,11-dihydro-11-[[(1-methyl-4-piperidinyl)-amino]-carbonyl]-6H-dibenz[b,e]azepin-6-one or a pharmacologically acceptable acid addition salt thereof with inorganic or organic acid.

3. The compound of claim 1 which is 5,11-dihydro-11-[(1-methyl-4-piperidinyl)-acetyl]-6H-dibenz[b,e]azepin-6-one or a pharmacologically acceptable acid addition salt thereof with an inorganic or organic acid.

4. The compound of claim 1 which is 5,11-dihydro-11-[(1-methyl-4-piperazinyl)-acetyl]-6H-dibenz[b,e]azepin-6-one or a pharmacologically acceptable acid addition salt thereof with an inorganic or organic acid.

5. A pharmaceutical composition containing as active ingredient a compound of claim 1 and pharmacologically acceptable carrier and/or diluent.

6. A process for treating a gastrointestinal tract condition in a warm-blooded host in need of such treatment which comprises administering to said host an effective amount of a compound of claim 1.

* * * * *